United States Patent [19]

Dawn

[11] Patent Number: 4,808,347
[45] Date of Patent: Feb. 28, 1989

[54] FAN DRIVEN AIR FRESHENER

[76] Inventor: Andrew R. Dawn, 713 Calle Contenta, San Clemente, Calif. 92672

[21] Appl. No.: 173,179

[22] Filed: Mar. 24, 1988

[51] Int. Cl.<sup>4</sup> .............................................. B01F 3/04
[52] U.S. Cl. ...................................... 261/30; 261/100; 261/DIG. 65; 422/124; 239/289; 239/57
[58] Field of Search .................. 422/124; 239/289, 57, 239/60, 30; 261/30, DIG. 65, 100

[56] References Cited

U.S. PATENT DOCUMENTS

| | | | |
|---|---|---|---|
| 3,006,042 | 10/1961 | Calandra | 219/472 |
| 3,576,593 | 4/1971 | Cicirello | 422/124 |
| 3,993,444 | 11/1976 | Brown | 261/DIG. 65 |
| 4,219,531 | 8/1980 | Wisniewski | 422/124 |
| 4,294,778 | 10/1981 | DeLuca | 261/30 |
| 4,339,079 | 7/1982 | Sato et al. | 239/57 |
| 4,604,245 | 8/1986 | Gutierrez | 261/30 |

Primary Examiner—Tim Miles
Attorney, Agent, or Firm—William L. Chapin

[57] ABSTRACT

An apparatus for freshening air within confined spaces such as the driver or passenger compartment of vehicles, or rooms within buildings, includes a housing which has an elongated cylindrical rear section adapted to plug into a standard cigarette lighter socket of the type commonly found in vehicles. An electric motor within the front section of the housing contains a propeller fastened to its shaft, the motor being powered through electrical contacts protruding through the rear section of the housing and contacting complementary contacts within the socket. A perforated dome-shaped cover removably fastenable to the larger diameter front section of the housing containing the propeller has a concave interior space adapted to hold a disposable scent producing an odor absorbing perforated disc.

15 Claims, 2 Drawing Sheets

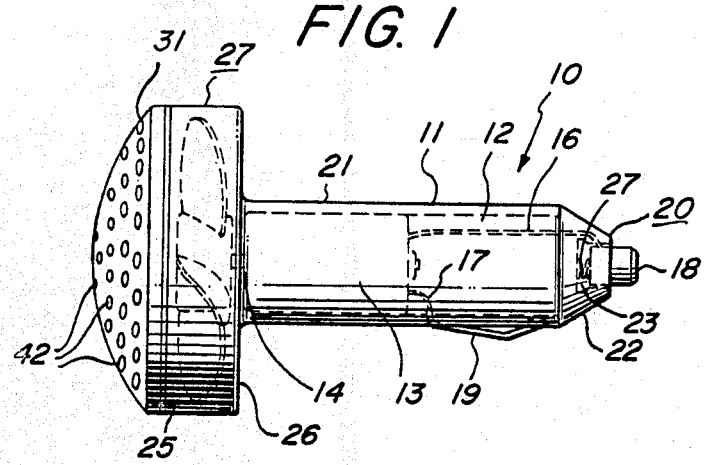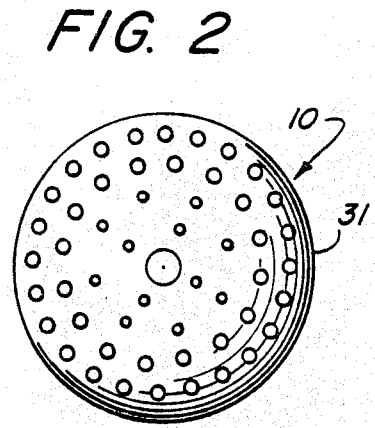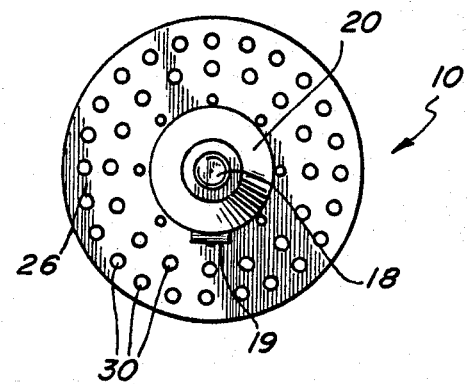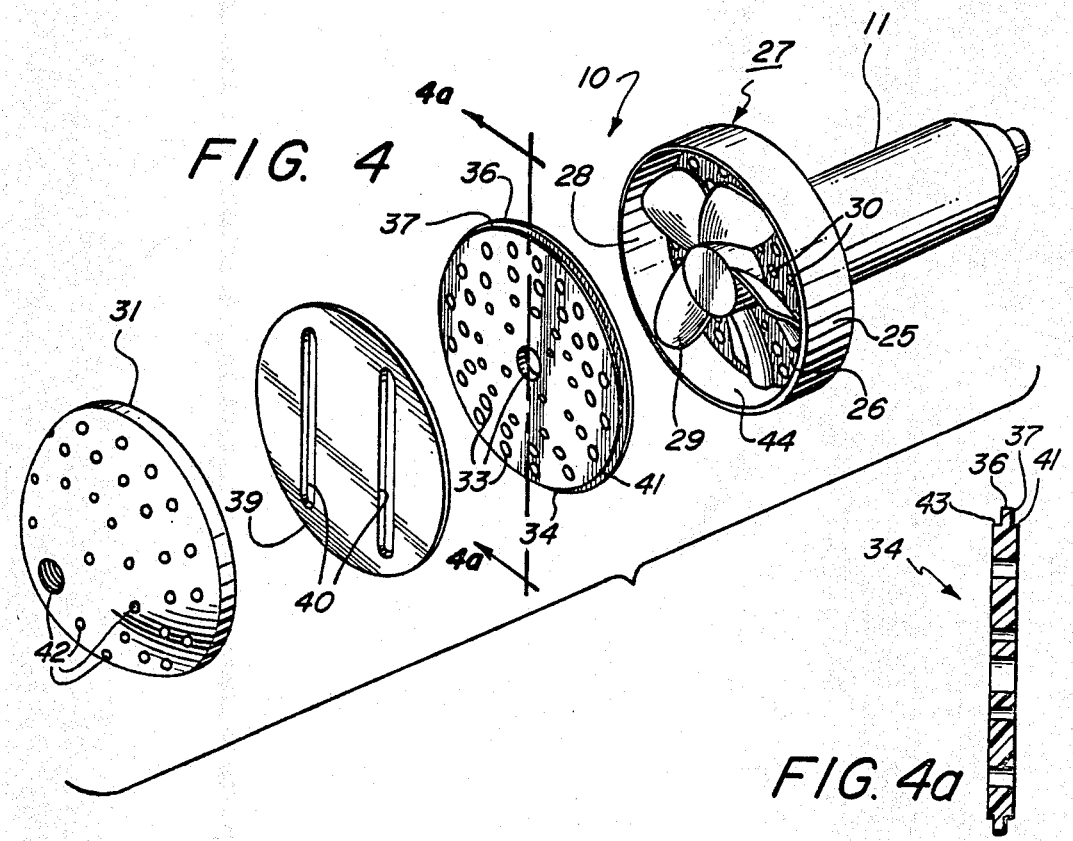

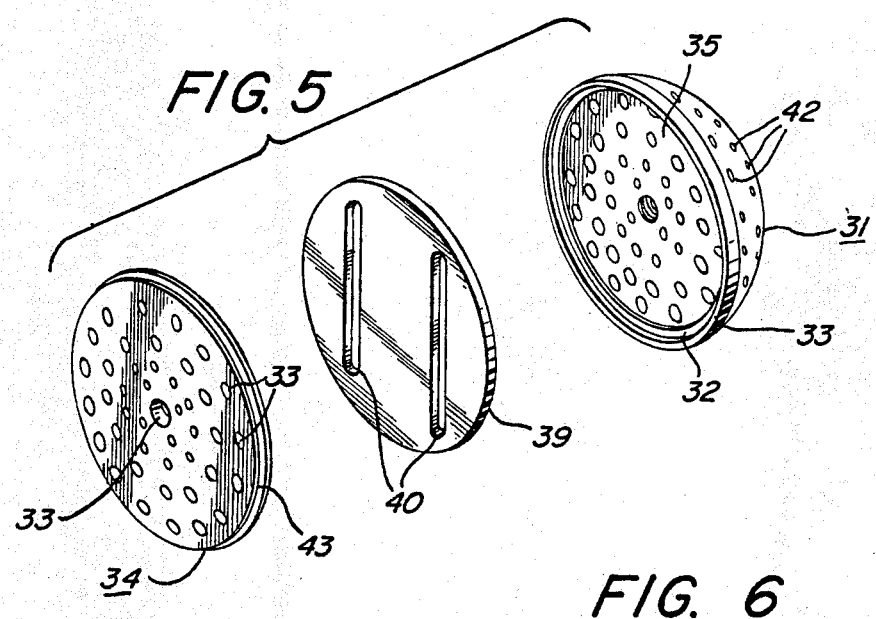
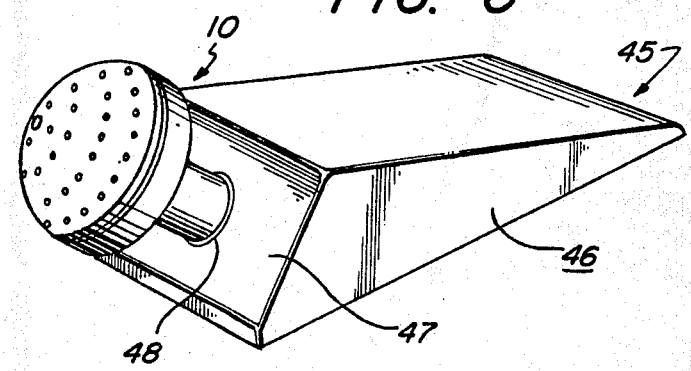
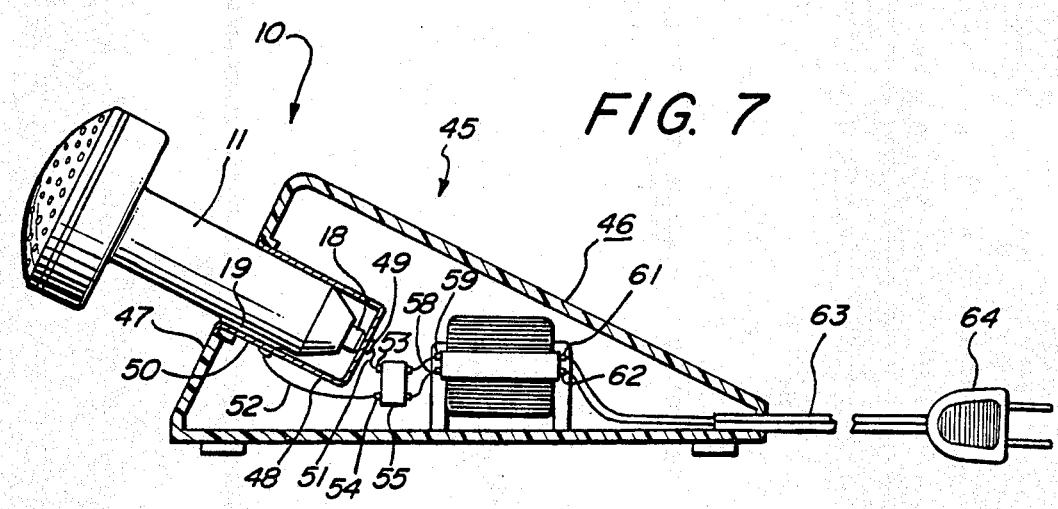

FAN DRIVEN AIR FRESHENER

BACKGROUND OF THE INVENTION

1. Field of the Invention

This invention relates to devices for deodorizing or perfuming air. More particularly, the invention relates to a portable device for freshening the air within a confined space such as found within the passenger compartment of a motor vehicle, or within a room.

2. Description of Background Art

The atmosphere within confined spaces occupied by people and animals frequently could benefit from the diminution of certain unpleasant odors. Thus, smoking, cooking and the activities of pets frequently cause unpleasant odors, which would desirably be absorbed or otherwise dissipated by some means, or at least replaced with a less objectionable perfume fragrance. Problems with odors are increased in structures which are tightly sealed against cold weather, or within closed motor vehicles where the inherently small air volume aggravates the effects of odorous agents. A number of devices have been disclosed which have as their intended purpose the reduction of unpleasant odors within buildings. Devices for controlling odors within automobiles are disclosed in the following U.S. Patents: U.S. Pat. Nos. 3,006,042, Calandra, Oct. 31, 1961, Auto Air Freshener, and 4,604,245, Gutierrez, Aug. 5, 1986, Perfume Dispensing Device.

The present invention was conceived of to provide a portable air freshener usable in buildings as well as automobiles and other motor vehicles.

OBJECTS OF THE INVENTION

An object of the present invention is to provide an air freshener which actively circulates air around an odor control element.

Another object of the invention is to provide an air freshener which employs a motor-driven fan to move air over an odor control element.

Another object of the invention is to provide a fan-driven air freshener which includes a readily replaceable odor control element.

Another object of the invention is to provide an air freshener which is useable both in vehicles and buildings, and which may be transported therebetween.

Various other objects and advantages of the present invention, and its most novel features, will be particularly pointed out in this disclosure.

It is to be understood that although the invention disclosed herein is fully capable of achieving the objects and providing the advantages mentioned, the structural and operational characteristics of the invention described herein are merely illustrative of the preferred embodiments. Accordingly, I do not intend that the scope of my exclusive rights and privileges in the invention be limited to the details of construction and operation described. I do intend that reasonable equivalents, adaptations and modifications of the invention described herein be included within the scope of the invention as defined by the appended claims.

SUMMARY OF THE INVENTION

Briefly stated, the present invention comprehends a device for freshening air within vehicles or rooms. The air freshener device according to the present invention has an elongated hollow cylindrical body containing an electrical motor, and external contacts adapted to provide electrical power to the motor when the body is plugged into a vehicle cigarette lighter socket.

The end of the elongated cylindrical body opposite the end containing external electrical contacts is enlarged to form a hollow boss coaxial with the body. A propeller within the boss is attached to the shaft of the electrical motor within the body, and is free to rotate within the boss. A perforated, convex end cap containing a perforated sheet saturated with scent closes the open end of the boss. Perforations through the back annular wall of the boss permit air flow through those perforations, through the perforated scent sheet, and through the perforated convex end wall of the end cap, providing effective dispersal into the atmosphere. Optionally, an accessory enclosure containing a cigarette lighter socket and a power conversion module with a line cord input for plugging into household electrical sockets permits using the air freshener devices indoors as well as in vehicles.

BRIEF DESCRIPTION OF THE DRAWINGS

FIG. 1 is a side elevation view of a fan-driven air freshener according to the present invention.

FIG. 2 is an upper plan view of the device of FIG. 1.

FIG. 3 is a lower plan view of the device shown in FIG. 1.

FIG. 4 is an exploded left end perspective of the device of FIG. 1.

FIG. 4A is a cross-sectional view of disc 34.

FIG. 5 is a fragmentary exploded right end perspective view of the device of FIG. 1.

FIG. 6 is a perspective view of the device of FIG. 1 combined with a housing providing electrical power to the device.

FIG. 7 is a longitudinal sectional view of the apparatus of FIG. 6, taken along the line 6—6 of that Figure.

DETAILED DESCRIPTION OF THE INVENTION

Referring now to FIGS. 1 through 5, and particularly to FIG. 1, a fan-driven air freshener 10 according to the present invention is shown. The air freshener 10 has an elongated cylindrical body 11, preferably made of a durable, electrically non-conductive material such as polypropylene. Preferably, body 11 is fabricated by injection molding.

As may be seen best by referring to FIG. 1, the interior space 12 of cylindrical body 11 contains an electric motor 13. The electric motor 13 has a generally cylindrical shape which fits coaxially within the hollow interior space 12 of the elongated cylindrical body 11, and an output shaft 14 extending forward from the front face 15 of the motor. Shaft 14 is axially aligned within the hollow cylindrical interior space 12 of the body 11. Preferably, this is accomplished by choosing the outer diameter of the motor relative to the inner diameter of body 11 so as to make the outer circumferential surface of the motor fit snugly within the body.

As shown in FIG. 1, electrical input power leads 16 and 17 from the motor 13 are connected to end and side electrical contacts 18 and 19, respectively, which protrude through the end and side walls 20 and 21 respectively of the cylindrical body 11. The end wall 20 of body 11 preferably has a tapering or beveled surface 22 which facilitates insertion of the body into a standard vehicle cigarette lighter socket. End contact 18 protruding coaxially outward through the end wall 20 of body 11 has a generally cylindrical shape, is axially slidably contained within a bore 23, and urged outward by a compression spring 27.

Side contact 19 has the shape of a rectangular strip, and is preferably made of a springy material such as phosphor bronze, so that the side contact, which is cantilevered out from a single attachment point through the side wall 21 of body 11, will be biased to an outward extending position, away from the body. Thus, when the body 11 is plugged into a cigarette lighter socket, both end contact 18 and side contact 19 will be spring biased into good electrical contact with complementary contacts within the socket, providing electrical power to motor 13.

As may be seen best by referring to FIGS. 1 and 4, the elongated cylindrical body 11 has at the end opposite end wall 20 an enlarged cylindrical flange 25 joined coaxially to the smaller diameter cylindrical side wall 21 of the body by a flat annular ring section 26.

Cylindrical flange 25 and annular ring section 26 together form an elongated hollow cylindrical boss section 27 at the end of cylindrical body 11. Preferably, boss section 27 is injection molded as an integral part of body 11.

As shown in FIGS. 1 and 4, the hollow interior space 28 of cylindrical boss section 27 accommodates a propeller or fan 29 attached to the output shaft 14 of electrical motor 13. As may be seen best by referring to FIG. 3, perforations 30 are provided through annular ring section 26 to permit free movement of air moved axially by the rotation of propeller 29.

As may be seen best by referring to FIGS. 1, 4 and 5, the hollow interior space 28 of hollow cylindrical boss section 27 is enclosed at its forward end by an outwardly convex, circular cross section, dome-shaped cap 31.

As may be seen best by referring to FIG. 5, an annular shoulder flange 32 of smaller diameter than the circular opening in the rear of dome-shaped cap 31 is located just forward, or just inside of, the rear transverse annular plane wall of the cap. As shown in FIGS. 1, 4 and 5, a generally flat circular cross-section plate 34 fits into the rear opening 35 of dome-shaped cap 31. Plate 34 is of the proper diameter to fit snugly within the rear opening 35 of cap 31 and rest on the annular shoulder flange 32 just inside the opening. Plate 34 has a larger diameter central flange 36 which forms an annular shoulder 37 adapted to butt against the rear annular wall 33 of the dome-shaped cap 31. Perforations 38 are provided through the thickness dimension of plate 34.

As shown in FIGS. 1, 4 and 5, the air freshener 10 includes a thin, replaceable scent disc 39 of generally circular shape. Scent disc 39 contains perforations 40 through its thickness dimension, and is made of cardboard, felt, or similar permeable material which has a large absorbtivity for liquid scents or deodorizers. The diameter of disc 39 is slightly less than the inner diameter of dome-shaped cap 31. Thus, disc 39 can be inserted into the rear opening in dome-shaped cap 31, and plate 34 then inserted into the opening. The interference fit between the smaller diameter front annular portion 41 of plate 34 with the opening 35 of dome-shaped cap 31 holds plate and cap together, and retains disc 39 between plate and cap.

As may be seen best by referring to FIG. 5, plate 34 contains on its rear surface a smaller diameter rear annular portion 43, of a proper size to form an interference fit with the inner circumferential surface of the front opening 44 of hollow cylindrical boss section 27. The interference fits between the front and rear smaller diameter portions of plate 34 with the dome-shaped cap 31 and boss section 27, repsectively, provide a convenient means for disassembling or reassembling the air freshener 10 without tools, and for replacing a scent disc after its scent has been dissipated.

The combination of the perforated flat annular ring section 26 of boss section 27, perforated plate 34, perforated scent disc 39, and perforated dome-shaped cap 31 provides a highly efficient means of directing air moved axially by propeller fan 39 to impinge on the scent disc, for the purpose of absorbing noxious odors from the atmosphere and replacing them with pleasant odors. Also, as described previously, the novel design of the air freshener 10 according to the present invention allows quick and easy removal and replacement of scent disc 39, without requiring tools.

FIGS. 6 and 7 illustrate a holder accessory which may be optionally combined with the air freshener 10 which provides a convenient means for operating the freshener inside a building. As shown in FIGS. 6 and 7, the holder accessory 45 includes an enclosure 46 having a front panel 47 through which is mounted a standard cigarette lighter socket 48 of the type commonly found in motor vehicles. Socket 48 contains an end contact 49 and a side contact 50 adapted to conductively contact end contact 18 and side contact 19, respectively, of cylindrical body 11 of freshener 10. Contacts 49 and 50 are electrically connected by wires 51 and 52 to the output terminals 53 and 54 of a full-wave bridge rectifier 55. The input terminals 56 and 57 of the full wave bridge rectifier are connected to the secondary terminals 58 and 59 of a step-down power transformer 60. The input terminals 61 and 62 of th power transformer are connected to a power cord 63 having at its opposite end a plug 64 adapted to plug into a standard 110 volt wall receptacle. Thus, accessory 45 may be used to provide 12 volt power to the air freshener 10 from household power lines, increasing the usefulness of the freshener by permitting it to be used indoors as well as in vehicles equipped with cigarette lighters.

What is claimed is:

1. An apparatus for freshening air within confined spaces comprising:
   (a) a housing having an elongated cylindrical end portion adapted to be inserted into an electrical power socket, said housing having external electrical contacts adapted to conductively contact internal electrical contacts within said socket,
   (b) an electrical motor contained within said housing, the input terminals of said motor being electrically coupled to said external contacts in a manner providing electrical power to said motor when said housing is plugged into said power socket,
   (c) an air displacing element fastened to the output shaft of said motor, said air displacing element being enclosed within said housing,
   (d) a perforated end cap covering said end of said housing opposite of said end containing external electrical contacts, said end cap adapted to removably attach to said housing and providing a space between said air displacing element and said perforations in said end cap for a thin sheet of odor absorbing, scent dispersing material.

2. The apparatus of claim 1 wherein said housing has an enlarged generally cylindrical, hollow cup-shaped end section opposite the elongated cylindrical end portion adapted to be plugged into an electrical power socket, said end section being coaxial with said elongated cylindrical end portion.

3. The apparatus of claim 2 wherein said perforated end cap has a generally dome-shaped convex exterior and a concave interior inwards of a rear circular opening of said cap.

4. The apparatus of claim 3 wherein said dome-shaped cap has an annular shoulder flange of smaller inner diameter than said circular rear opening of said cap, said flange located slightly inwards of the rear transverse annular end wall of said cap.

5. The apparatus of claim 4 further including a perforated circular plate of the proper diameter to fit snugly within said rear opening of said cap and rest on said annular shoulder flange, thereby providing between the inner plane surface of said plate and the inner concave surface of said cap a space for scent releasing material.

6. The apparatus of claim 5 wherein said perforated plate has a large diameter center flange which forms an annular shoulder adapted to butt against the rear annular wall of said dome-shaped cap.

7. The apparatus of claim 6 wherein said perforated plate has a smaller diameter rear annular portion of the proper size to fit snugly within the front opening of said hollow cup-shaped end section of said housing.

8. The apparatus of claim 7 wherein said air displacing element is coaxially overlain by said cup-shaped end section.

9. The apparatus of claim 8 wherein said rear portion of said enlarged hollow cup-shaped end section joined to said elongated cylindrical portion of said housing contains perforations communicating within the hollow interior of said cup-shaped section.

10. The apparatus of claim 9 wherein said air displacing element is further defined as a propeller.

11. The apparatus of claim 5 wherein said scent releasing material is a generally disc-shaped perforated, thin sheet of absorbent material impregnated with scent, said diameter of said disc being smaller than smaller diameter entrance of said dome-shaped cap.

12. An apparatus for freshening air within a confined space comprising;
(a) an elongated circular transverse cross-section housing having an elongated hollow cylindrical rear section and a shorter, larger diameter hollow front section coaxial with said rear section, said cylindrical rear section adapted to be inserted into an electrical power socket, and including external electrically conductive elements protruding through said cylindrical rear section adapted to resiliently engage coplementary internal contacts within said socket,
(b) a generally cylindrical electrical motor contained in a generally coaxial position within the hollow interior space of said elongated hollow cylindrical rear section, each of the electrical power terminals of said motor being conductively connected to a separate one of said external conductive elements,
(c) a propeller fastened to the output shaft of said motor, said propeller located coaxially within said larger diameter front section of said housing, and
(d) a generally circular cross-section dome-shaped end cap removably fastenable coaxially to said front section of said housing, thereby enclosing said front section and providing a space for a thin sheet of odor absorbing material, said end cap containing a plurality of axially disposed perforations communicating with the interior space of said front section.

13. The appartus of claim 12 wherein said larger diameter front section of said housing has an annular rear transition section joined to the elongated smaller diameter rear section of said housing, said annular rear transition section provided with a plurality of axially disposed perforations communicating with the hollow exterior of said front section.

14. The apparatus of claim 13 further including a thin circular plate perforated through its thickness dimension, the front surface of said plate adapted to removably press fit into the rear opening of said dome-shaped cap and forming a generally hemispherical-shaped chamber therewithin adapted to hold circular, perforated scent impregnated discs, and the rear surface of said plate adapted to removably press fit into the front opening of said front section of said housing.

15. The apparatus of claim 12 further including an accessory having a panel mounting an electrical power socket adapted to receive said cylindrical rear section of said apparatus, said panel having internal electrical contacts adapted to conductively couple to said external contacts, said electrical contacts being operatively connected to a source of electrical power.

* * * * *